United States Patent
del Real Pena et al.

(10) Patent No.: US 11,975,169 B2
(45) Date of Patent: May 7, 2024

(54) SYMMETRIC TUBING CLAMPS

(71) Applicant: Fresenius Medical Care Holdings, Inc., Waltham, MA (US)

(72) Inventors: Diego Suarez del Real Pena, Mission, TX (US); Nelson Guillermo Santiago Velazquez, Reynosa (MX)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 149 days.

(21) Appl. No.: 17/328,122

(22) Filed: May 24, 2021

(65) Prior Publication Data

US 2022/0370783 A1 Nov. 24, 2022

(51) Int. Cl.
*A61M 39/28* (2006.01)
*A61M 1/14* (2006.01)
*A61M 1/36* (2006.01)

(52) U.S. Cl.
CPC .............. *A61M 39/28* (2013.01); *A61M 1/14* (2013.01); *A61M 1/36* (2013.01); *A61M 1/367* (2013.01);
(Continued)

(58) Field of Classification Search
CPC .... A61M 1/14; A61M 1/1694; A61M 1/1698; A61M 1/32; A61M 1/34; A61M 1/36; A61M 1/3621; A61M 1/3624; A61M 1/367; A61M 1/3692; A61M 1/38; A61M 2039/0009; A61M 2202/0021; A61M 2202/0413; A61M 2205/0216; A61M 2210/12; A61M 39/28; A61M 39/284; A61M 1/0259; A61M 1/0272; A61M 1/0281; F16K 7/06; F16K 7/063
See application file for complete search history.

(56) References Cited

U.S. PATENT DOCUMENTS 7,892,197 B2    2/2011  Folden et al.
9,555,232 B2 *  1/2017  Davis .................... F16K 7/04
(Continued)

FOREIGN PATENT DOCUMENTS

EP          3028738       6/2016
WO    WO 2015/062101     5/2015

OTHER PUBLICATIONS advantapure.com [online], "Single-Use Tubing Assemblies," retrieved on Jul. 22, 2021, retrieved from URL <http://advantapure.com/single-use-systems.htm>, 5 pages.
(Continued)

*Primary Examiner* — Shefali D Patel
(74) *Attorney, Agent, or Firm* — Fish & Richardson P.C.

(57) ABSTRACT

This disclosure relates to symmetric tubing clamps for blood treatment systems and related systems and methods. In some aspects, a tubing clamp includes a resilient body that has symmetry with respect to a first plane with a normal along a longitudinal axis of the resilient body, the resilient body comprising a sidewall defining an opening such that a tubing is arrangeable through the opening along the longitudinal axis of the resilient body; first and second snap-fit features configured to engage with each other when the resilient body is compressed along a direction transverse to the longitudinal axis; and a protrusion configured to constrict the tubing when the resilient body is compressed along the direction transverse to the longitudinal axis.

20 Claims, 10 Drawing Sheets

(52) U.S. Cl.
CPC ... *A61M 1/3621* (2013.01); *A61M 2202/0021* (2013.01); *A61M 2202/0413* (2013.01); *A61M 2210/12* (2013.01)

(56) References Cited

U.S. PATENT DOCUMENTS

| | | | | |
|---|---|---|---|---|
| 2012/0245555 | A1* | 9/2012 | Spickermann | A61M 1/3621 604/500 |
| 2015/0285404 | A1 | 10/2015 | Koyama et al. | |
| 2017/0120040 | A1* | 5/2017 | Burkholz | A61M 39/288 |

OTHER PUBLICATIONS alibaba.com [online], "Big Large Hose Tube Adjustable Flow Control Roller Regulator Clamp," retrieved on Jul. 22, 2021, retrieved from URL <https://www.alibaba.com/product-detail/10mm-Adjustable-enema-tube-roller-regulator_60605566648.html>, 5 pages.

alibaba.com [online], "Plastic Medical Pipe Hose Slide Clip Slide Clamp for 0.5~10mm Tubing in Hospital," retrieved on Jul. 22, 2021, retrieved from URL <https://www.alibaba.com/product-detail/Plastic-medical-pipe-hose-slide-clip_60616621675.html>, 8 pages.

amazon.com [online], "Gas Tapper G.I Power Equipment Fluid Extractor Pump for Gas, Oil, Water, Anti-Freeze Great on Lawnmowers, Power Equipment, Motorcycles—USA Assembly & Hose," retrieved on Jul. 22, 2021, retrieved from URL <https://www.amazon.com/GasTapper-Power-Equipment-Model-filter/dp/B00TA5ECJQ/ref=pd_lpo_2?pd_rd_i=B00TA5ECJQ&psc=1>.

belart.com [online], "Jaw Style Tubing Clamp," retrieved on Jul. 16, 2021, retrieved from URL <https://www.belart.com/jaw-style-tubing-clamp.html>, 2 pages.

gogenlab.com [online], "BEL-ART F18218-0000 Tubing Pinch Clamp for Tubing up to 1/2-in O.D.," retrieved on Jul. 22, 2021, retrieved from URL <https://www.gogenlab.com/lab-supplies/clamps/tubing-clamps/tubing-pinch-clamp/bel-art-f18218-0000-tubing-pinch-clamp-tubing-1>, 4 pages.

gogenlab.com [online], "Tubing Pinch Clamp," retrieved on Jul. 22, 2021, retrieved from URL <https://www.gogenlab.com/lab-supplies/clamps/tubing-clamps/tubing-pinch-clamp/tubing-pinch-clamp>, 3 pages.

hobbyhomebrew.com [online], "Tubing Clamp 5 Pack Medium 12-Position Siphon Hose Pinch Type Shut off Clamp for Flexible Tubing," retrieved on Jul. 22, 2021, retrieved from URL <https://www.hobbyhomebrew.com/product/tubing-clamp-5-pack-medium-12-position-siphon-hose-pinch-shut-off/>, 9 pages.

leybold-shop.com [online], "Tubing clamp, 6 mm," retrieved on Jul. 22, 2021, retrieved from URL <https://www.leybold-shop.com/biology/biology-chemistry-catalogue/laboratory-aids/tubing/tubing-clamp-6-mm-604441.html>, 2 pages.

preiser.com [online], "Plastic Tubing Clamp for Tubing under 3/4" O.D. 6/PK," retireved on Jul. 22, 2021, retrieved from URL <https://www.preiser.com/plastictubingclampfortubingunder34od6pk.aspx>, 2 pages.

tblplastics.com [online], "Bio-Ease HD | Single-Use Pinch Clamp for Tubing," retrieved on Jul. 22, 2021, retrieved from URL <https://www.tblplastics.com/fittings/tubing-hose-clamp-bio-ease-hd/>, 6 pages.

thomassci.com [online], "Keck Ramp Clamp Tubing Clamps," retrieved on Jul. 22, 2021, retrieved from URL <https://www.thomassci.com/Equipment/Clamps-Supports/_/Keck-Ramp-Clamp-Tubing-Clamps>, 2 pages.

usplastic.com [online], "Acetal Tubing Clamps," retrieved on Jul. 22, 2021, retrieved from URL <https://www.usplastic.com/catalog/item.aspx?itemid=84302&clickid=related-slider>, 3 pages.

usplastic.com [online], "Blue 6 Position Polypropylene Tubing Clamp for Tubing up to 0.45" OD," retrieved on Jul. 22, 2021, retrieved from URL <https://www.usplastic.com/catalog/item.aspx?itemid=121992>, 5 pages.

usplastic.com [online], "Delrin® Screw Clamp for tubing up to 1/2"(14mm) OD," retrieved on Jul. 22, 2021, retrieved from URL <https://www.usplastic.com/catalog/item.aspx?itemid=84244&clickid=recommended-slider>, 4 pages.

usplastic.com [online], "KECK™ Ramp Tubing Clamps," retrieved on Jul. 22, 2021, retrieved from URL <https://www.usplastic.com/catalog/item.aspx?itemid=23246>, 3 pages.

usplastic.com [online], "Screw Clamp 3 Pack," retrieved on Jul. 22, 2021, retrieved from URL <https://www.usplastic.com/catalog/item.aspx?itemid=84301&catid=858>, 3 pages.

usplastic.com [online], "Tubing Clamps," retrieved on Jul. 22, 2021, retrieved from URL <https://www.usplastic.com/catalog/item.aspx?itemid=23098&catid=858>, 6 pages.

International Search Report and Written Opinion in International Appln. PCT/US2022/030324, dated Aug. 19, 2022, 16 pages.

International Preliminary Report on Patentability in International Appln. No. PCT/US2022/030324, dated Dec. 7, 2023, 9 pages.

\* cited by examiner

SYMMETRIC TUBING CLAMPS

TECHNICAL FIELD

This disclosure relates to symmetric tubing clamps for blood treatment systems.

BACKGROUND

Dialysis is a treatment used to support a patient with insufficient renal function. The two principal dialysis methods are hemodialysis and peritoneal dialysis. During hemodialysis, the patient's blood is passed through a dialyzer of a blood treatment machine while also passing a dialysis solution or dialysate through the dialyzer.

A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the blood treatment machine acts as an artificial kidney for cleansing the blood.

SUMMARY

In one aspect, a tubing clamp includes a resilient body that has symmetry with respect to a first plane with a normal along a longitudinal axis of the resilient body. The resilient body includes a sidewall defining an opening such that a tubing is arrangeable through the opening along the longitudinal axis of the resilient body. The resilient body includes first and second snap-fit features configured to engage with each other when the resilient body is compressed along a direction transverse to the longitudinal axis. The resilient body includes a protrusion configured to constrict the tubing when the resilient body is compressed along the direction transverse to the longitudinal axis.

In another aspect, a blood treatment system includes a blood treatment machine and a disposable line set configured to be coupled to the blood treatment machine. The disposable line set includes a fluid line configured to be connected to a patient for treating blood of the patient and a tubing clamp including a resilient body that has symmetry with respect to a first plane with a normal along a longitudinal axis of the resilient body. The resilient body includes a sidewall defining an opening such that the fluid line of the disposable line set is arranged through the opening along the longitudinal axis of the resilient body. The resilient body includes first and second snap-fit features configured to engage with each other when the resilient body is compressed along a direction transverse to the longitudinal axis. The resilient body includes a protrusion configured to constrict the fluid line of the disposable line set when the resilient body is compressed along the direction transverse to the longitudinal axis.

In a further aspect, a method includes applying a force to at least one of a top member and a bottom member of a tubing clamp to move the top and bottom members of the tubing clamp toward each other to compress a tubing disposed in the tubing clamp and constrict fluid flow within the tubing. The method includes engaging a first snap-fit feature of the tubing clamp with a second snap-fit feature of the tubing clamp to maintain the compression of the tubing when the force is released, the first snap-fit feature being part of the top member and the second snap-fit feature being part of the bottom member. The method includes shearing the top member relative to the bottom member to release the compression of the tubing and release the constriction of fluid flow in the tubing.

Implementations can include one or more of the following features.

In some implementations, the resilient body has symmetry with respect to a second plane with a normal perpendicular to the longitudinal axis.

In some implementations, the first and second snap-fit features each comprise an angled face. The angled face of the first snap-fit feature is configured to engage the angled face of the second snap-fit feature when the resilient body is compressed along the direction transverse to the longitudinal axis.

In some implementations, the protrusion extends transverse to the longitudinal axis of the resilient body.

In some implementations, the protrusion comprises a semi-circular cross section.

In some implementations, the resilient body comprises a face comprising grip features.

In some implementations, the opening is elliptical-shaped.

In some implementations, the resilient body has symmetry with respect to a second plane with a normal perpendicular to the longitudinal axis.

In some implementations, the tubing clamp has symmetry with respect to a first plane with a normal direction along a longitudinal axis of the tubing clamp.

In some implementations, the tubing clamp has symmetry with respect to a second plane with a normal direction perpendicular to the longitudinal axis.

In some implementations, the movement of the top member and the bottom member of the tubing clamp toward each other generates strain energy within the tubing clamp.

In some implementations, the movement of the top member and the bottom member of the tubing clamp toward each other is caused by the force being applied in a direction perpendicular to a longitudinal axis of the tubing clamp.

In some implementations, moving the top and bottom members of the tubing clamp apart from each other after the top member is sheared relative to the bottom member restores the tubing clamp to an initial position of the tubing clamp.

In some implementations, shearing the top member relative to the bottom member causes a displacement of the top member relative to the bottom member along a longitudinal axis of the tubing clamp.

In some implementations, shearing the top member relative to the bottom member causes a displacement of the first snap-fit feature relative to the second snap-fit feature.

In some implementations, shearing the top member relative to the bottom member causes a disengagement of the first snap-fit feature from the second snap-fit feature.

In some implementations, inserting an end of the tubing through an opening at a first end of the tubing clamp and then inserting the end of the tubing through an opening at a second end of the tubing clamp arranges the tubing within the tubing clamp.

In some implementations, constricting the fluid flow within the tubing includes constricting a flow of blood of a patient within the tubing.

Implementations can include one or more of the following advantages.

A symmetric tubing clamp can be used to clamp a fluid line independently of an orientation of the clamp with respect to the fluid line. This means that a user can use his/her thumb to close the tubing clamp regardless of a direction that the tubing clamp is installed on the fluid line. This avoids confusion by a user since there is no preferred orientation direction of the symmetric tubing clamps described herein. In contrast, some conventional asymmetric clamps are designed to align with the user's thumb in one direction. Grabbing these asymmetric clamps in the opposite direction would feel odd to the user and could lead to confusion. In some cases, there is a higher chance of breaking these asymmetric clamps if the user forces the clamp to close while grabbing it in this incorrect orientation. Typically the user would need to reorient their body and/or the tubing so he/she can grab the clamp in the correct orientation. This can be an uncomfortable experience for the user. The symmetric tubing clamps described herein are usable regardless of their orientation on the fluid line and do not have the above noted deficiencies of asymmetric clamps.

A symmetric tubing clamp with snap-fit features is able to produce an audible "snap" sound as well as haptic feedback when switched into a closed configuration. This audible and haptic feedback reassures the user that the fluid line is properly closed and that blood from the patient and/or a blood treatment system is not going to leak past the symmetric tubing clamp.

The symmetric tubing clamp can have a resilient body providing sufficient flexibility such that the tubing clamp can be operated with one hand. For example, the user can squeeze the tubing clamp using his/her thumb and index finger to switch the tubing clamp from an open configuration (where the fluid line is not occluded) to a closed configuration (where the fluid line is occluded). Additionally, the user can shear the tubing clamp using his/her same thumb and index finger to switch the tubing clamp from the closed configuration back to the open configuration. This is an advantage over many conventional tubing clamps that require the user to use two hands.

A symmetric tubing clamp with a resilient body is able to store elastic energy in the form of strain energy. This allows the symmetric tubing clamp to spring back into the open configuration when locking engagement between the snap-fit features is released. Such a symmetric tubing clamp is user-friendly since all that is needed to return the tubing clamp to the open configuration is a shearing action to release the locking engagement between the snap-fit features.

In some cases, the symmetric tubing clamp is a monolithic device. The claim can, for example, be molded out of a single thermoplastic material. Such monolithic clamps are advantageous over tubing clamps that require multiple parts because the monolithic clamps have fewer parts and do not require assembly. Additionally, this reduces the chance of introducing human errors by assembling multiple parts together. In some cases, human errors can be so bad that the errors require a re-working of the clamp and/or requiring the clamp to be completely discarded. In some cases, human errors may not be noticed until the clamp is in service which can expensive and embarrassing to resolve.

The symmetric tubing clamps described herein can be manufactured and assembled without requiring the tubing clamp to be arranged in a specific orientation. On the other hand, if an asymmetric clamp is not oriented per the requirements of the engineering drawings, the asymmetric clamp would need to be re-worked causing a waste of time, resources, and money. The symmetric tubing clamps described herein do not have this issue because they are symmetric and do not require the tubing clamp to be arranged in specific orientation during manufacturing and assembly.

The symmetric tubing clamps described herein can be used with various medical systems. For example, the symmetric tubing clamps can be used in peritoneal dialysis and in any other medical device requiring the occlusion of a line.

Other aspects, features, and advantages will be apparent from the description and drawings, and from the claims.

DETAILED DESCRIPTION

This disclosure relates generally to symmetric tubing clamps for fluid management. For example, the symmetric tubing clamps can be used in blood treatment systems. Symmetric tubing clamps include one or more planes of symmetry and can be used independently of their orientation. Symmetric tubing clamps can, for example, be used on blood lines of a disposable set for blood treatment machines to control the flow of blood between the patient and the blood treatment machine.

Figure 1:
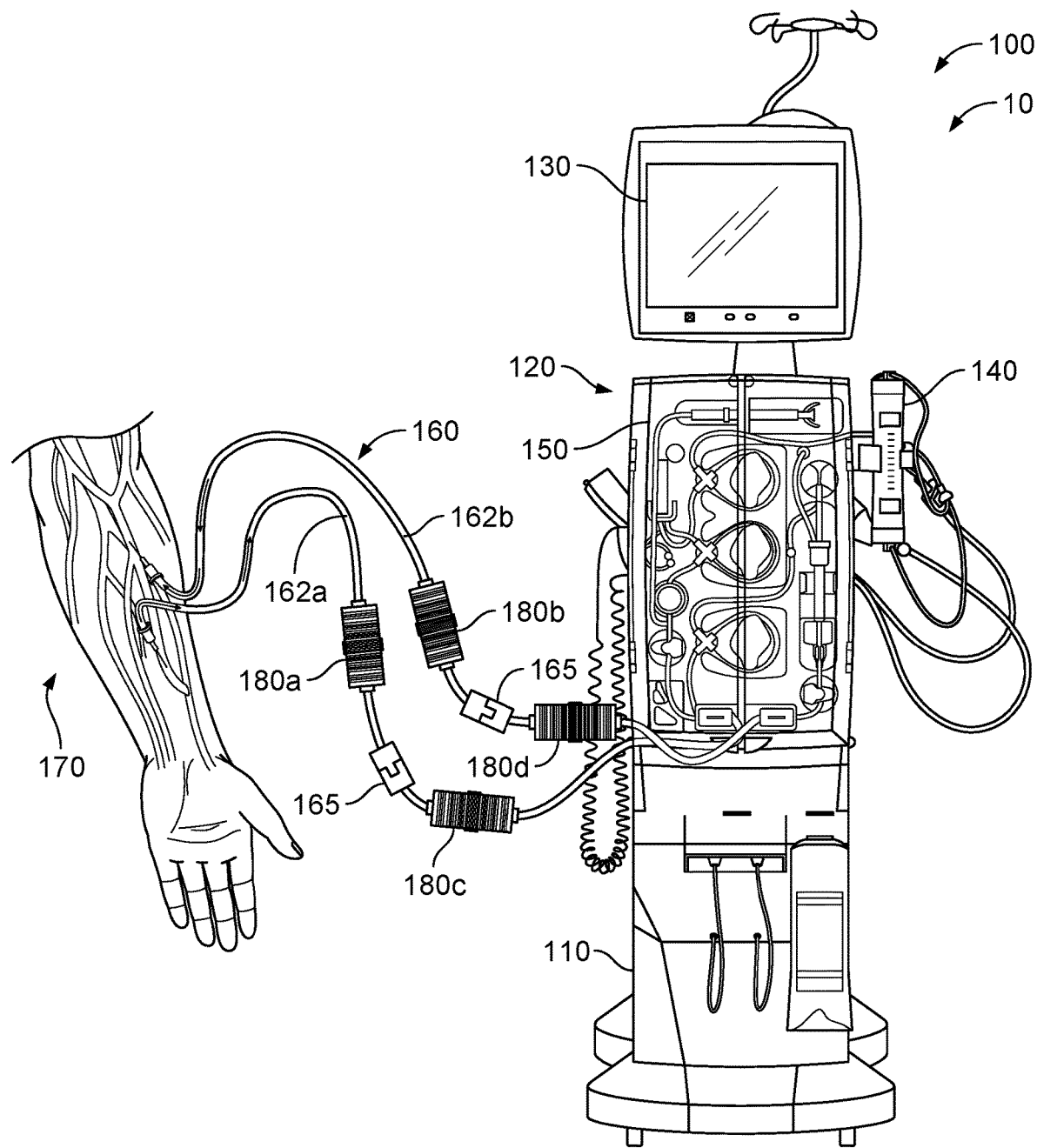
FIG. 1 shows a blood treatment machine with a blood line connected to a patient.

Referring to FIG. 1, a blood treatment system 10 includes a blood treatment machine 100 and a disposable blood line set 160 (also referred to as a disposable set 160) that can be connected to the blood treatment machine 100, as shown in FIG. 1. The blood treatment machine 102 includes a base 110, an extracorporeal blood module 120, and a user interface 130. The blood treatment machine 100 includes electronic circuitry and a processor in electrical communication with the user interface 130. The user interface 130 can be a color touch screen display. Doors 150 are connected via hinges to the blood treatment machine 100 and enable a user to obtain access to the extracorporeal blood module 120 by opening the doors 150. The doors 150 can be transparent to enable a user to see the extracorporeal blood module 120 through the doors 150 when the doors 150 are in a closed configuration (as shown in FIG. 1).

Still referring to FIG. 1, the disposable set 160 includes arterial and venous fluid lines 162a, 162b connected to a patient 170, as well as other fluid lines and components that are connected to the extracorporeal blood module 120 of the blood treatment machine 100. The disposable set 160 also includes a dialyzer 140 that is fluidly connected to the arterial and venous fluid lines 162a, 162b. The disposable set 160 includes connectors 165 that allow portions of the fluid lines connected to the patient 170 to be disconnected from portions of the fluid lines connected to the blood treatment machine 100.

Figure 2:
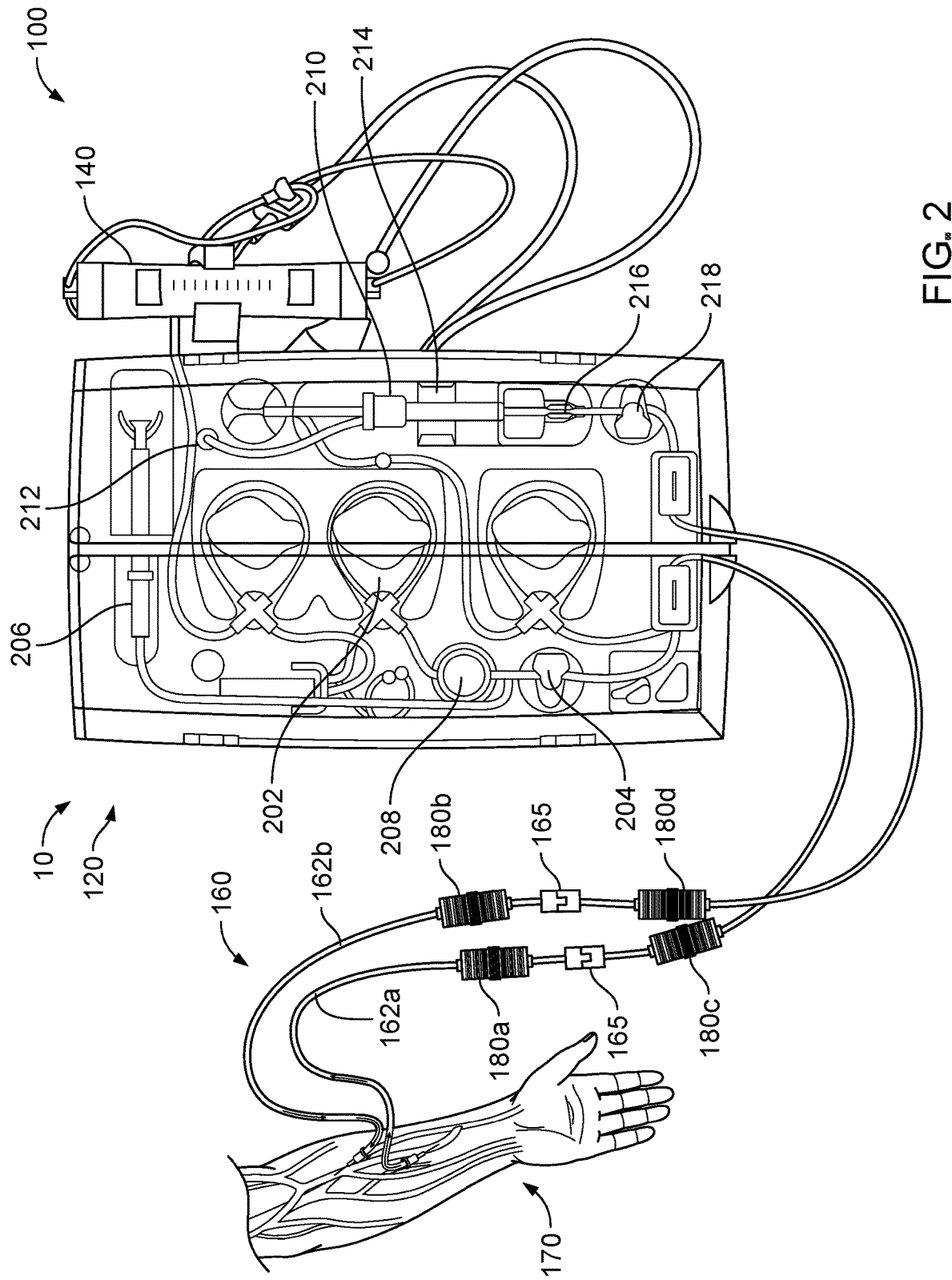
FIG. 2 shows an extracorporeal blood module of the blood treatment machine of FIG. 1.

In operation, the arterial fluid line 162a and the venous fluid line 162b of the disposable set 160 are connected to the arm of the patient 170 and blood is pumped from the patient 170 using a blood pump 202 of the extracorporeal blood module 120 (as shown in FIG. 2). The blood flows from the patient 170, through the arterial fluid line 162a, the dialyzer 140, the venous fluid line 162b, and then back to the patient 170. As the blood flows through one compartment of the dialyzer 140, dialysate is pumped through an adjacent compartment of the dialyzer 140 to clean (e.g., remove toxins from) the blood. Further details of the blood treatment machine 100 are described with reference to FIG. 2 below.

As shown in FIG. 1, the arterial and venous fluid lines 162a, 162b of the disposable set 160 include symmetric tubing clamps 180a-180d. The tubing clamps 180a-180d are used to compress the arterial and venous fluid lines 162a, 162b and constrict the flow of blood within the arterial and venous fluid lines 162a, 162b. In some cases, the tubing clamps 180a-180d completely stop the flow of blood through the arterial and venous fluid lines 162a, 162b when the tubing clamps 180a-180d are in a closed configuration and allow unrestricted flow of blood through the arterial and venous fluid lines 162a, 162b when the tubing clamps 180a-180d are in an open configuration.

Specifically, the tubing clamps 180a, 180b allow the patient 170 to be disconnected from the blood treatment machine 100 (by disconnecting the connectors 165) without loss of the patient's blood through the connectors 165 when the tubing clamps 180a, 180b are in the closed configuration. Additionally, the tubing clamps 180c, 180d allow the patient 170 to be disconnected from the blood treatment machine 100 (by disconnecting the connectors 165) without blood dripping from the connectors 165 when the tubing clamps 180a, 180b are in the closed configuration. In this way, tubing clamps can be used on either side of the connectors 165 and more than one tubing clamp can be used on each of the arterial and venous fluid lines 162a, 162b.

Generally, the tubing clamps 180a-180d are installed by inserting them onto their respective arterial and venous fluid lines 162a, 162b via an open end of the arterial and venous fluid lines 162a, 162b at the connectors 165. The tubing clamps 180a-180d are symmetric so they can be used in any directional orientation. In other words, the tubing clamps 180a-180d can be flipped with respect to the arterial and venous fluid lines 162a, 162b and still function properly. The tubing clamps 180a-180d can be installed along the arterial and venous fluid lines 162a, 162b and can be operated (e.g., switched from the open configuration into the closed configuration and vice versa) with one hand.

Once the tubing clamps 180a-180d are located along their respective arterial and venous fluid lines 162a, 162b and the patient end portions of the arterial and venous fluid lines 162a, 162b are connected to the rest of the arterial and venous fluid lines 162a, 162b via the connectors 165, the tubing clamps 180a-180d are switched into their open configurations to allow blood to flow to and from the patient 170 via the arterial and venous fluid lines 162a, 162b. Then the blood treatment machine 100 can be instructed to begin blood treatment (e.g., via the user interface 130). The tubing clamps 180a-180d can be subsequently closed by the user during pauses in the blood treatment and closed after the blood treatment is complete. Once the blood treatment is complete, the patient 170 can be disconnected from the blood treatment machine 100 and the tubing clamps 180a-180d can be removed from the arterial and venous fluid lines 162a, 162b and reused for the next patient. Additional details regarding the tubing clamps 180a-180d are described with reference to FIGS. 3A-3D below.

Referring to FIG. 2, during blood treatment with the blood treatment machine 100, the blood pump 202 is operated to draw blood from the patient 170 into the arterial fluid line 162a of the disposable set 160. The blood flows through the open arterial clamp 204. A heparin syringe 206 is connected to the arterial fluid line 162a and is used to inject heparin into the blood as the blood flows through the arterial fluid line 162a. The blood then flows through an arterial pressure measurement unit 208, through the peristaltic blood pump 202, and then flows to the dialyzer 140 where the blood is filtered. The filtered blood exits the dialyzer 140 via the venous fluid line 162b of the disposable set 160 and flows to a venous drip chamber 210. A venous pressure measurement unit 212 is connected to the venous drip chamber 210 via a pigtail line for measuring the blood pressure within the venous drip chamber 210. A level detector 214 partially surrounds the venous drip chamber 210 for detecting the blood level within the venous drip chamber 210. The blood exits the bottom of the venous drip chamber 210 and flows through the venous optical detector and air bubble detector 216, the open venous clamp 218, and back to the patient 170.

FIGS. 3A-3D show perspective and plan views of the symmetric tubing clamp 180a disposed on the arterial fluid line 162a. FIGS. 4A and 4B show perspective and plan views, respectively, of the symmetric tubing clamp 180a alone. Specifically, FIG. 4B is a cross-section view showing the tubing clamp 180a when cut through the plane 380 shown in FIG. 3D. It will be understood that clamps 180b-180d are identical to clamp 180a. As such, clamps 180b-180d will not be separately described in detail. Similarly, the venous fluid line 162b on which the clamps 180b and 180d are disposed has the same general structure as the arterial fluid line 162a and thus will not be separately described in detail.

Referring to FIGS. 3A-3D and FIGS. 4A and 4B, the symmetric tubing clamp 180a includes a resilient body 300 that can be deformed (compressed, sheared, etc.) under the force exerted by fingers of a user. The resilient body 300 includes opposing sidewalls 302 that define an opening 304 such that the arterial fluid line 162a is arrangeable through each opening 304 along a longitudinal axis 306 of the resilient body 300. The openings 304 are elliptical-shaped. The arterial fluid line 162a is a hollow tube of resilient plastic such that it is deformable by the tubing clamp 180a. The longitudinal axis 306 of the resilient body 300 is aligned with the 'X' axis of the coordinate system 350.

Figure 3A:
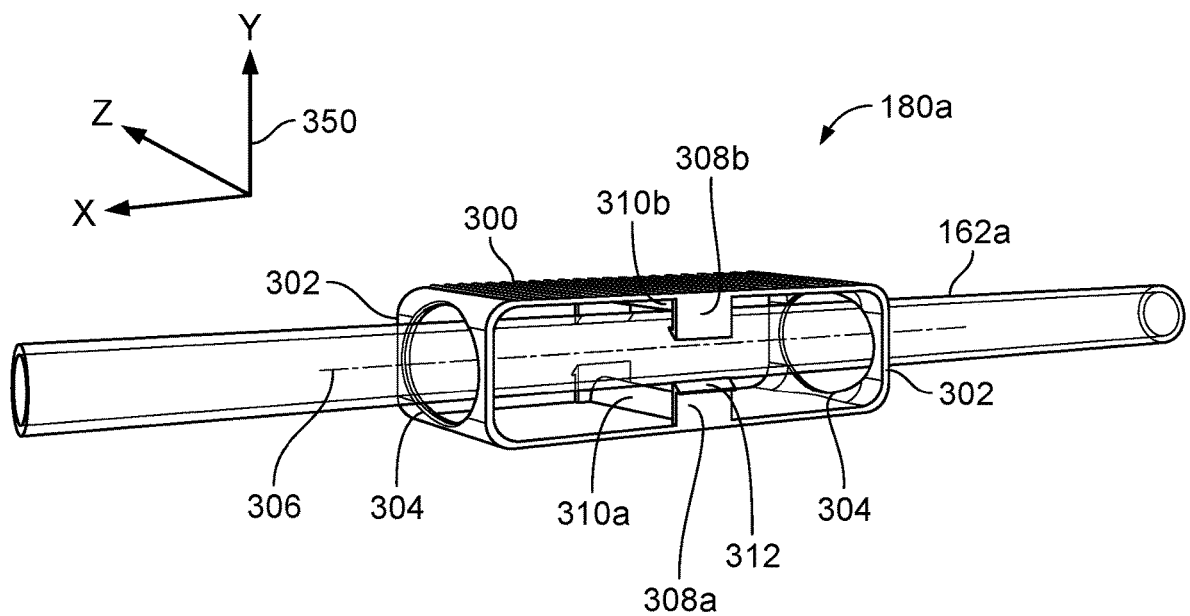
FIGS. 3A-3D show perspective and plan views of a blood line passing through a symmetric tubing clamp.
Figure 3B:
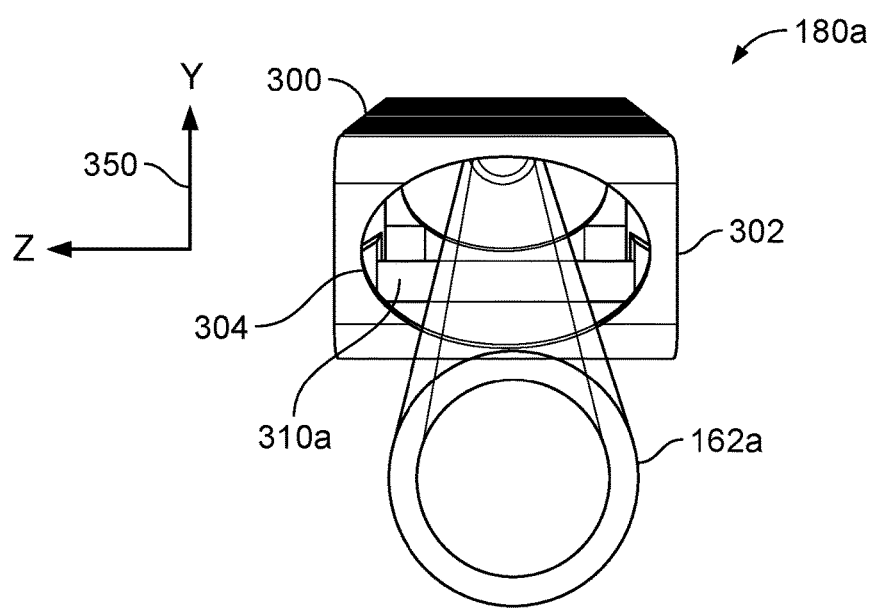
Figure 3C:
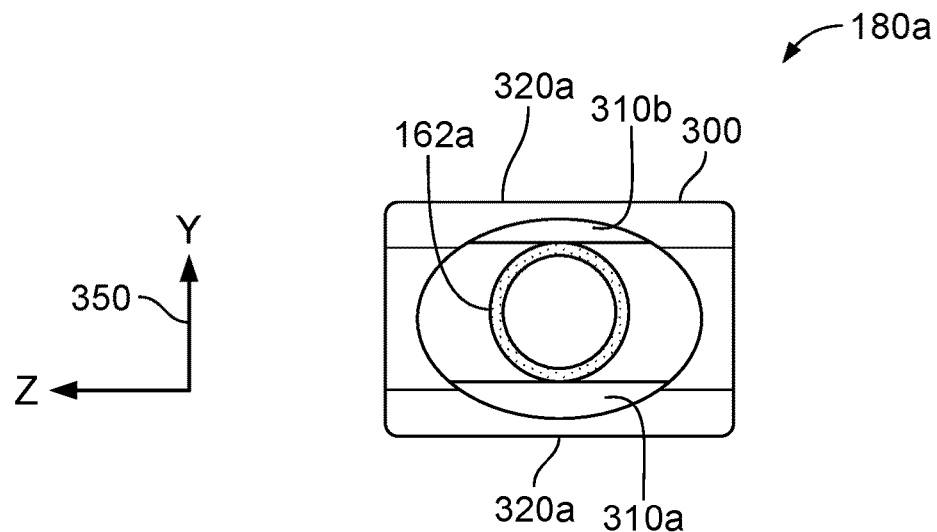
Figure 4A:
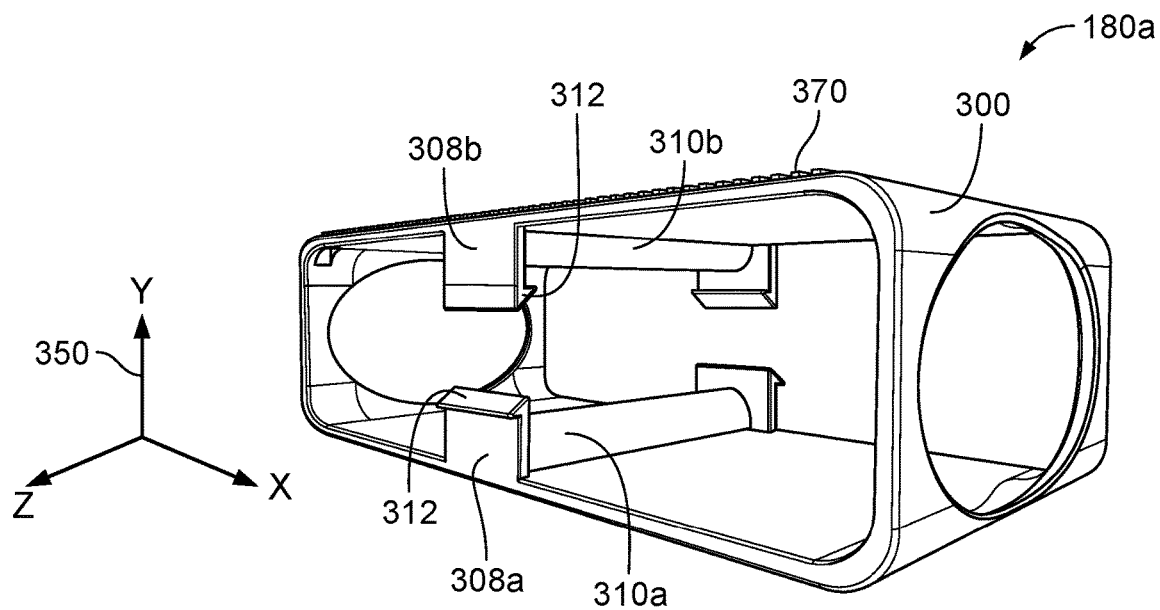
FIGS. 4A and 4B show perspective and plan views, respectively, of the symmetric tubing clamp of FIGS. 3A-3D.
Figure 4B:
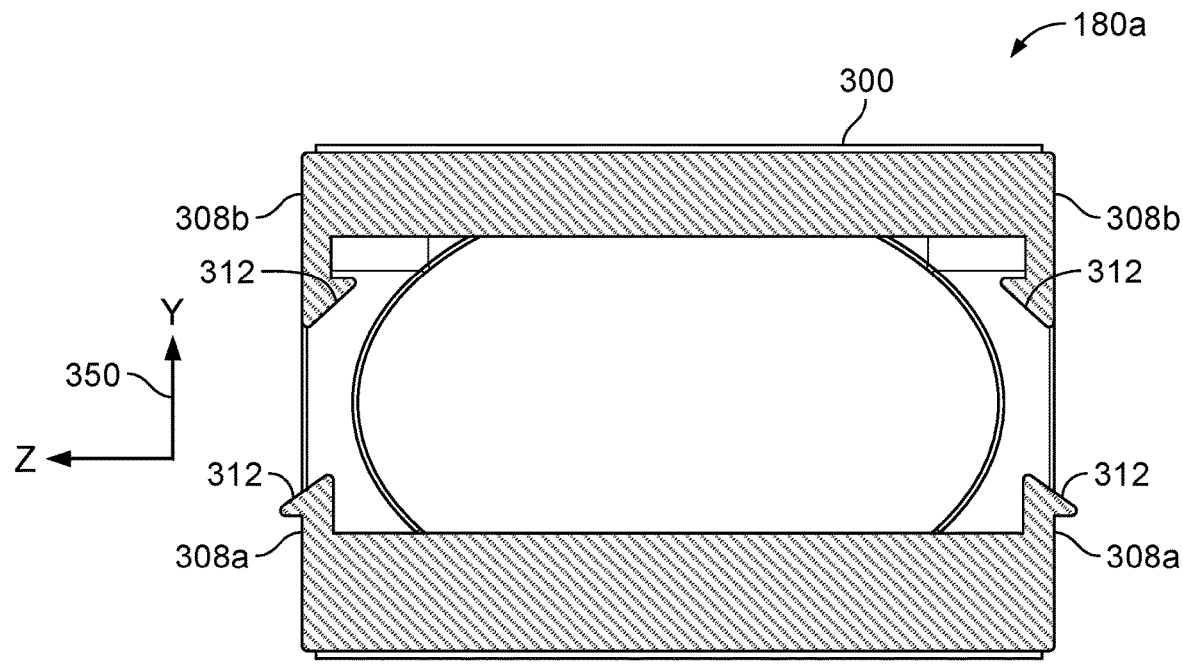

As shown in FIGS. 3A, 4A, and 4B, the resilient body 300 includes a snap-fit feature 308a and a complementary snap fit-feature 308b configured to engage with each other when the resilient body 300 is compressed along the 'Y' axis of the coordinate system 350. In other words, the snap-fit features 308a, 308b engage each other when the resilient body 300 is compressed along a direction transverse to the longitudinal axis 306. The snap-fit feature 308a and the complementary snap-fit feature 308b are hook shaped and each include an angled face 312 configured to engage each other.

The resilient body 300 includes a pair of protrusions 310a, 310b configured to constrict or pinch the fluid line 162a when the resilient body 300 is compressed along the 'Y' axis. The protrusions 310a, 310b extend along the 'Z' direction of the coordinate system 350. In other words, the protrusions 310a, 310b extend transverse to the longitudinal axis 306 of the resilient body 300. The protrusions 310 also include a semi-circular cross section. Each end of the protrusion 310a, 310b intersects the snap-fit features 308.

Figure 3D:
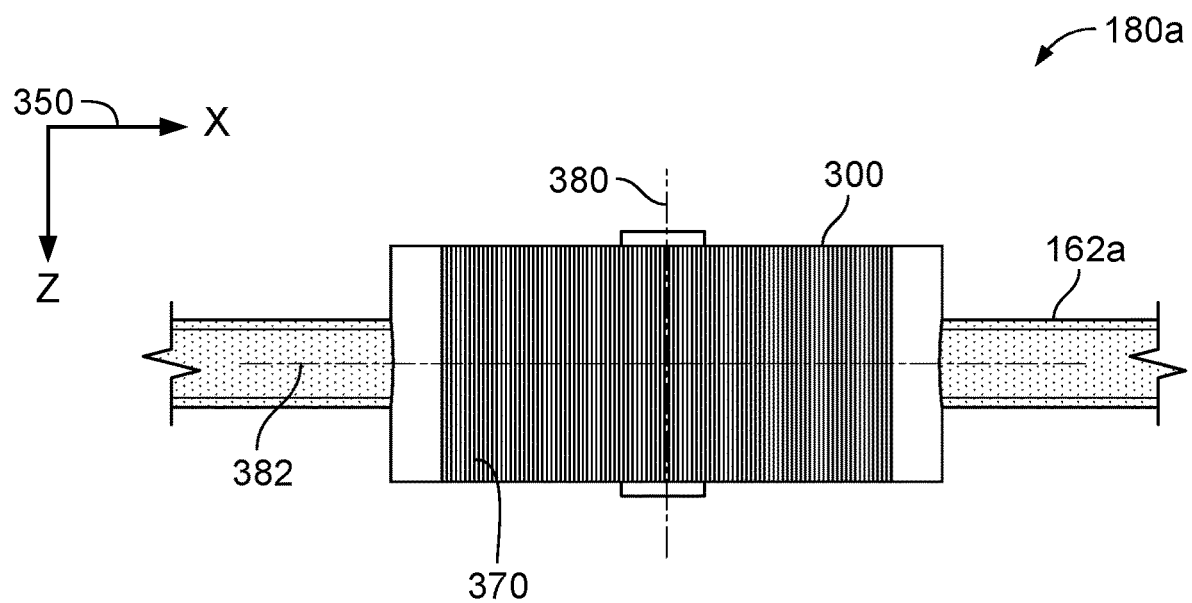

Referring to FIGS. 3D and 4A, the resilient body 300 includes grip features 370 that allow a user to grip the tubing clamp 180 with their fingers and switch the symmetric tubing clamp 180a between the open configuration and the closed configuration. The grip features 370 include a plurality of grooves equally spaced and aligned along the 'Z' direction. Both a top face 320a and a bottom face 320b of the resilient body 300 include the grip features 370. The grip features 370 are in the form of a knurled outer surface of the resilient body 300 in the illustrated embodiment.

As shown in FIG. 3D, the resilient body 300 has symmetry with respect to a first plane 380 with a normal along the longitudinal axis 306. The resilient body 300 also has symmetry with respect to a second plane 382 with a normal perpendicular to the longitudinal axis 306. These planes of symmetry allow the tubing clamp 180a to be used independent of orientation with respect to the fluid line 162a.

Figure 5A:
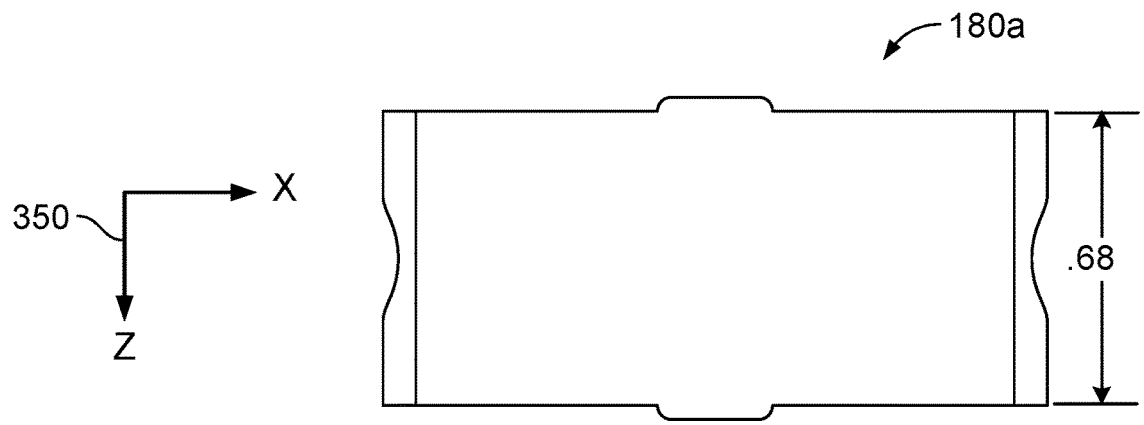
FIGS. 5A-5C show additional plan views of the symmetric tubing clamp of FIGS. 3A-3D.
Figure 5B:
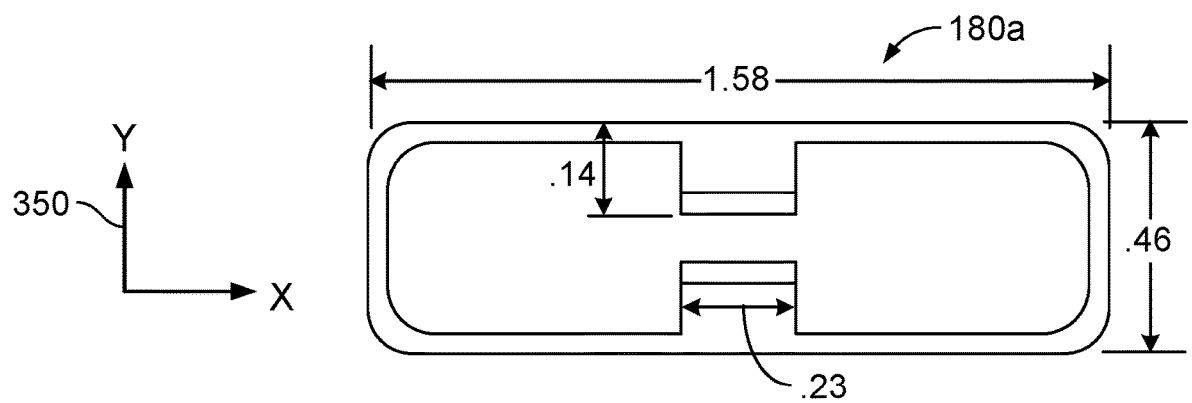
Figure 5C:
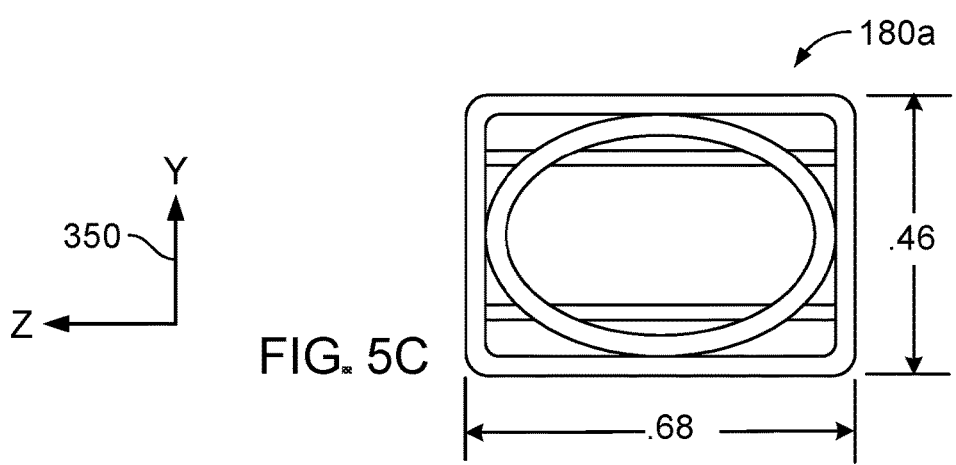

FIGS. 5A-5C show additional plan views of the symmetric tubing clamp 180a. Specifically, FIGS. 5A-5C show nominal dimensions of the tubing clamp 180a. Referring to FIG. 5A, a width measured along the 'Z' axis of the tubing clamp 180a is nominally 0.68 inches. Referring to FIG. 5B, a height measured along the 'Y' axis of the tubing clamp 180a is nominally 0.46 inches and a length measured along the 'X' axis of the tubing clamp 180a is nominally 1.58 inches. A length of the snap-fit features 308a, 308b measured along the 'X' axis is nominally 0.23 inches and a height of the snap-fit features 308a, 308b measured along the 'Y' axis is nominally 0.14 inches. FIG. 5C shows the nominal width of 0.68 inches and the nominal height of 0.46 inches from an alternative view.

Figure 6A:
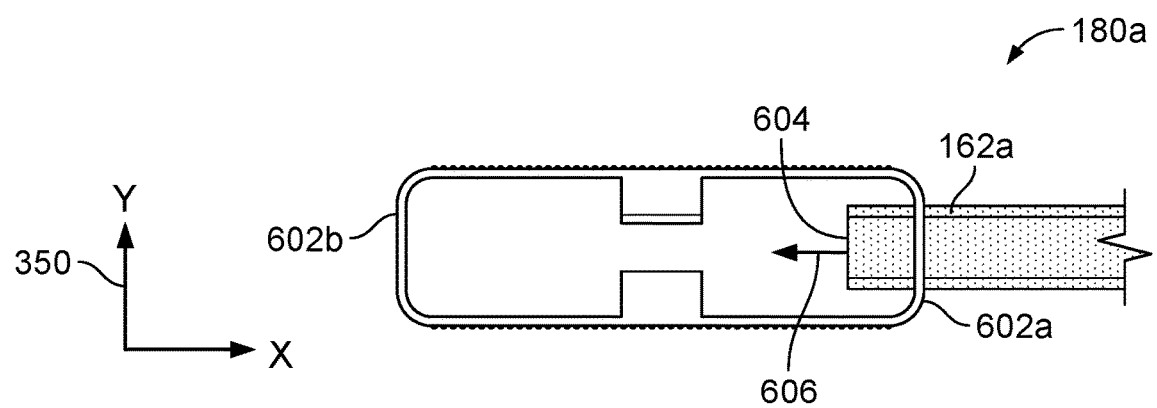
FIGS. 6A-6E show a sequence of side views of the symmetric tubing clamp of FIGS. 3A-3D during operation.
Figure 6B:
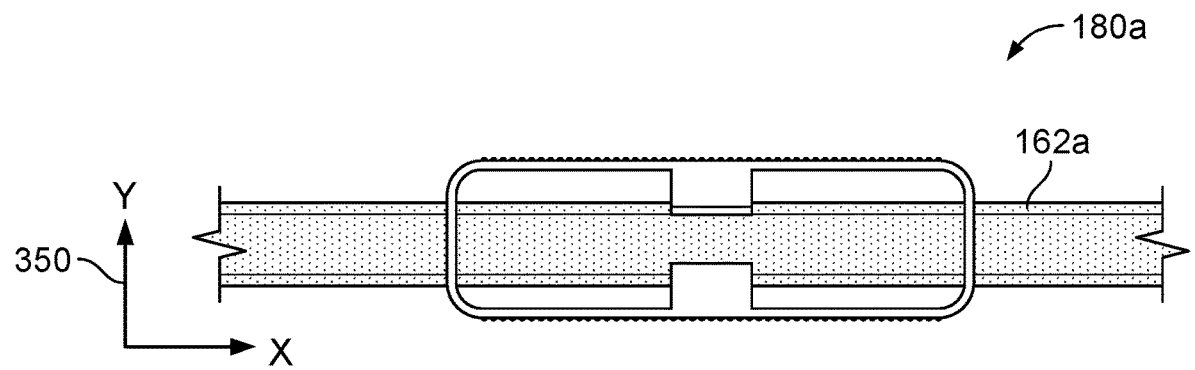

FIGS. 6A-6E show a sequence of side views of the symmetric tubing clamp 180a during use. First, a user inserts an end 604 of the arterial fluid line 162a through an opening on a first side 602a of the tubing clamp 180a in a direction of the arrow 606, and inserts the end 64 of the arterial fluid line 162a through an opening on a second side 602b of the tubing clamp 180a. FIG. 6B shows the arterial fluid line 162a after it is inserted through the tubing clamp 180a. As described with reference to FIGS. 1 and 2 above, one portion of the arterial fluid line 162a is configured to be attached to the blood treatment machine 100 and another portion of the arterial fluid line 162a is configured to be attached to the patient 170. FIGS. 6A and 6B show the tubing clamp 180a in the open configuration where flow in the arterial fluid line 162a is not restricted by the tubing clamp 180a.

Figure 6C:
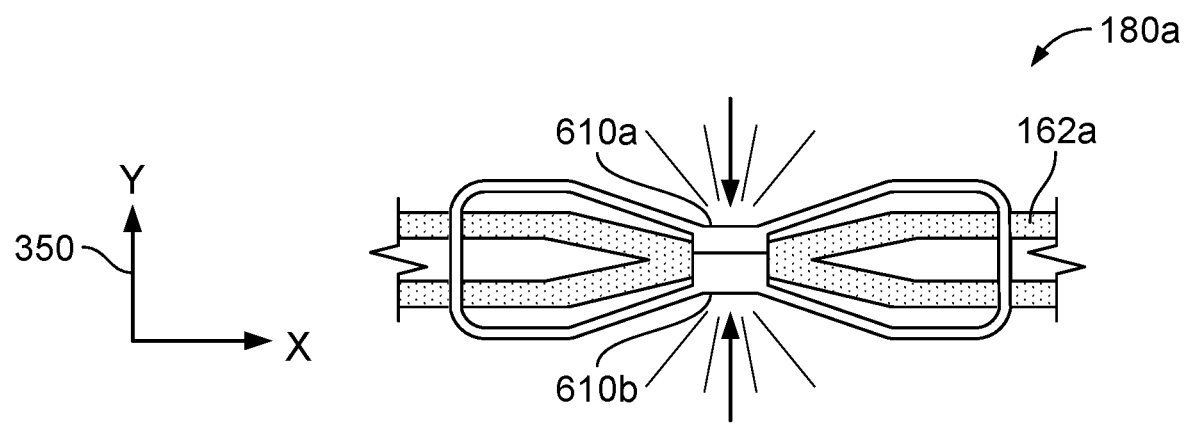
Figure 6D:
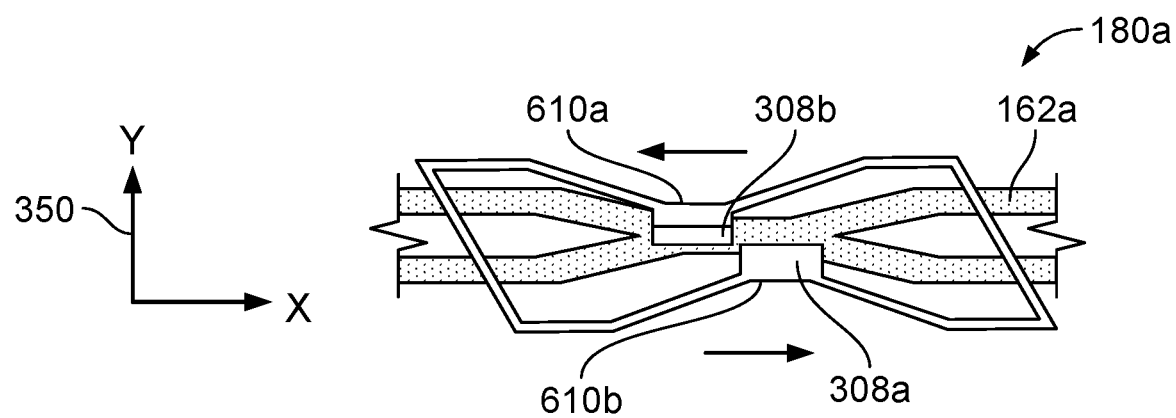

Once the tubing clamp 180a is installed on the fluid line 162a, the user can close the tubing clamp 180a to compress the fluid line 162a and constrict flow within the fluid line 162a. Referring to FIG. 6C, the user can deflect a top face 610a of the tubing clamp 180a and a bottom face 610b of the tubing clamp 180a toward each other from an initial position. For example, the user can use their fingers to generate a compression force to deflect the top face 610a toward the bottom face 610b. In some cases, the user can pinch a center of the top face 610a and a center of the bottom face 610b to cause the deflection.

As the top face 610a and the bottom face 610b deflect toward each other, the protrusions 310a, 310b approach each other. This causes the protrusions 310a, 310b to compress the fluid line 162a which constricts the flow within the fluid line 162. Additionally, as the top face 610a and the bottom face 610b deflect toward each other, the angled faces 312 of the snap-fit feature 308a and the complementary snap-fit feature 308b also engage each other. Since the angled faces 312 are oriented such that they oppose each other, when the angled faces 312 engage they cause the snap-fit feature 308a and the complementary snap-fit feature 308b to resiliently deform and snap into locking engagement. In some cases, an audible "snap" can be heard when the snap-fit feature 308a and the complementary snap-fit feature 308b snap into engagement.

FIG. 6C shows the tubing clamp 180a in the closed configuration. Once in engagement, the mechanical connection of the engagement between the snap-fit feature 308a and the complementary snap-fit feature 308b maintains the compression of the fluid line 162a when the force applied by the user is released. In other words, the user can step away from the tubing clamp 180a and the tubing clamp 180a will remain in the closed configuration due to the engagement between the snap-fit feature 308a and the complementary snap-fit feature 308b.

To switch the tubing clamp 180a back into the open or initial configuration, the user can use their fingers to shear the top face 610a relative to the bottom face 610b to release the compression of the tubing and release the constriction of flow in the tubing 162a. For example, referring to FIG. 6D, the user can shear the bottom face 610b along the direction of the positive 'X' axis and the top face 610a along the direction of the negative 'X' axis. As the tubing clamp 180a shears, the snap-fit feature 308a slides out of engagement with the complementary snap-fit feature 308b.

It will be understood that the clamps 180b-180d can be disposed on their associated arterial and venous lines 162a, 162b and operated in the same way as the clamp 180a described above.

Figure 6E:
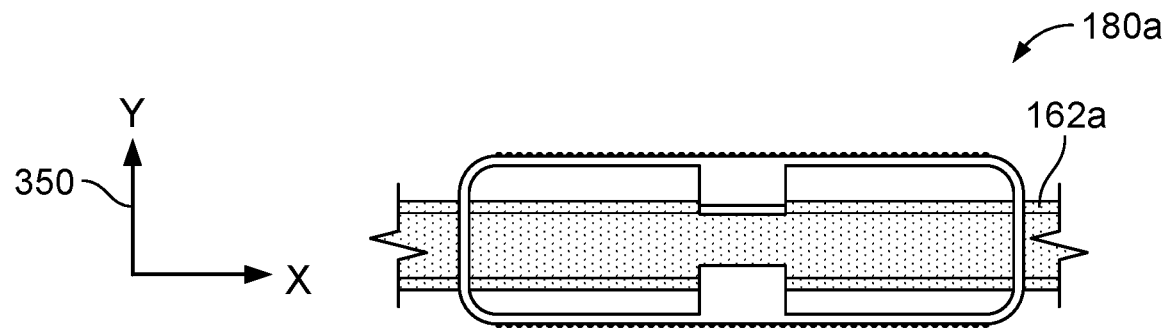

Additionally, the deflection of the top face 610a and the bottom face 610b of the tubing clamp 180a toward each other generates strain energy within the tubing clamp. This allows the tubing clamp 180a to "spring" back to its initial position after the snap-fit feature 308a and the complementary snap-fit feature 308b are disengaged by shearing the top face 610a relative to the bottom face 610b. As a result, the tubing clamp 180 returns to its initial position as shown in FIG. 6E. In the initial position, the fluid line 162a is no longer constricted by the tubing clamp 180a and fluid is allowed to flow between the patient 170 and the blood treatment machine 100.

While certain examples have been described, other examples are possible.

Figure 7A:
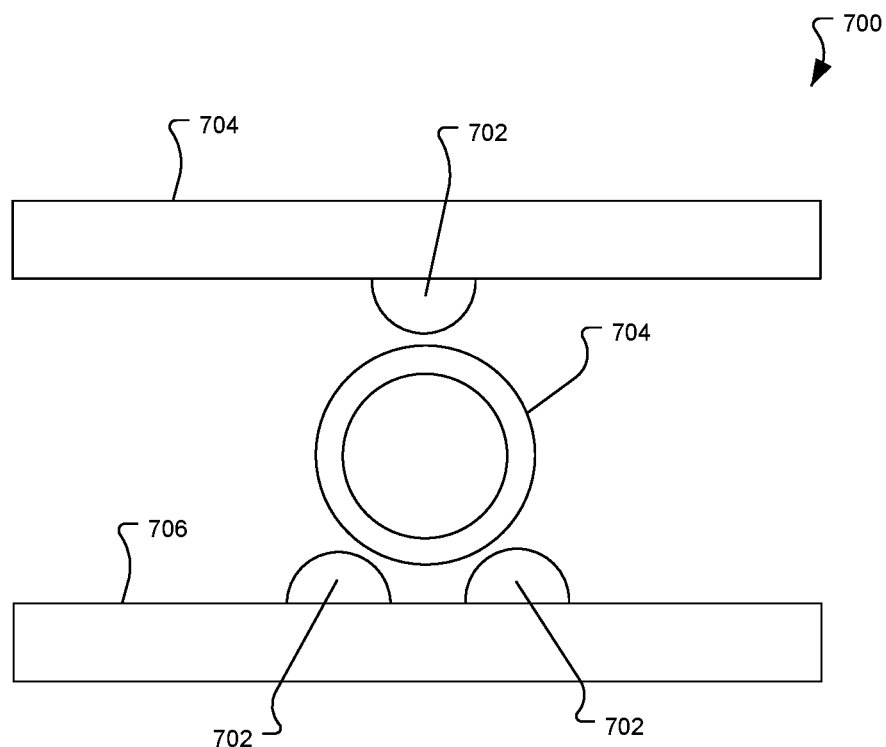
FIGS. 7A and 7B show a symmetric tubing clamp with three protrusions in an open state and closed state, respectively.
Figure 7B:
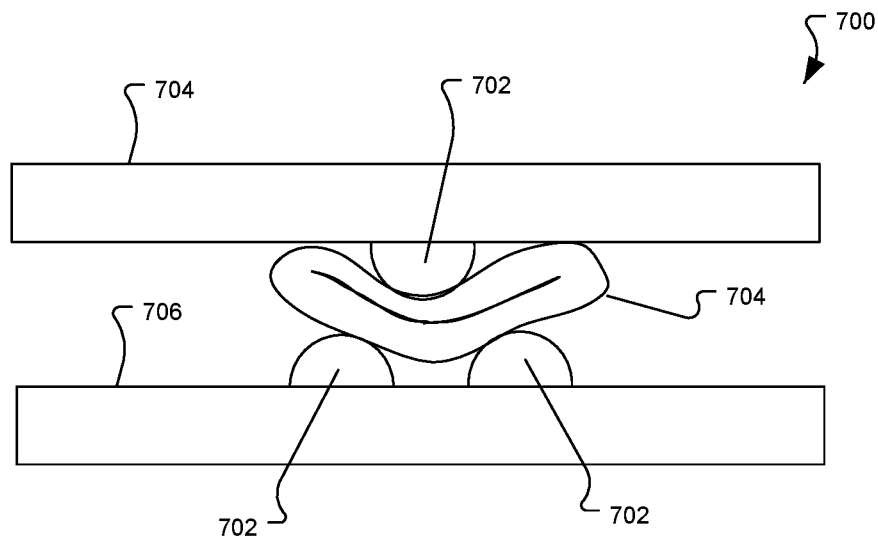

While tubing clamps 180a-180d have been described as including two protrusions 310a, 310b that interact to close the fluid line 162a, more than two protrusions can be used. For example, FIGS. 7A and 7B show a tubing clamp 700 with three protrusions 702 arranged in a triangular configuration. Other than the three protrusions 702, tubing clamp 700 is substantially the same as tubing clamp 180. Referring to FIG. 7A, a top face 704 of the tubing clamp 700 has one protrusion 702 and a bottom face 706 of the tubing clamp 700 has two protrusions 702. This allows the tubing clamp 700 to constrict the flow differently than tubing clamp 180. A snap-fit feature similar to the snap-fit features 308a, 308b is used to hold the tubing clamp 700 in a closed configuration (not explicitly shown in FIGS. 7A and 7B).

Figure 8A:
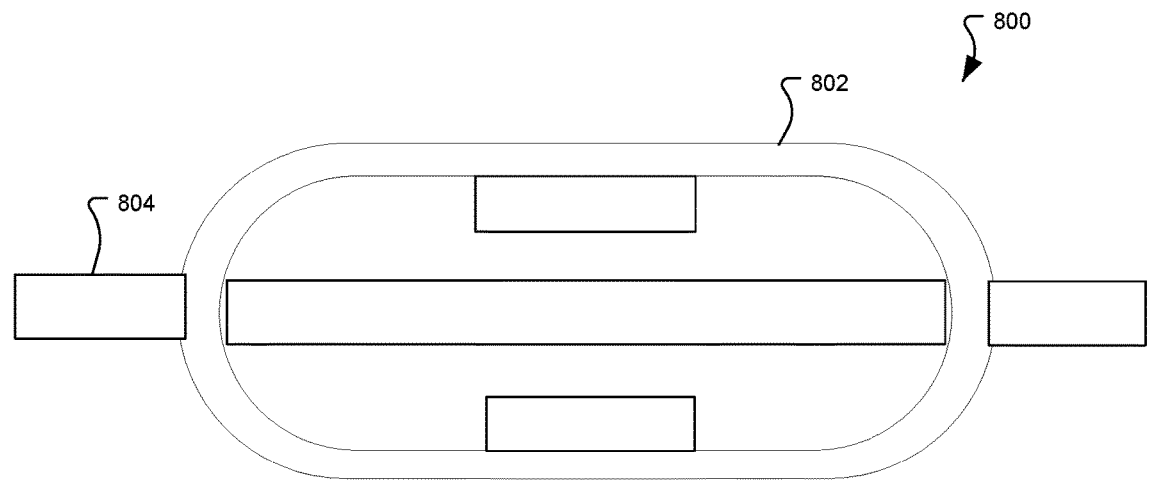
FIGS. 8A and 8B show a symmetric tubing clamp with an elliptical-shaped resilient body in an open state and closed state, respectively.
Figure 8B:
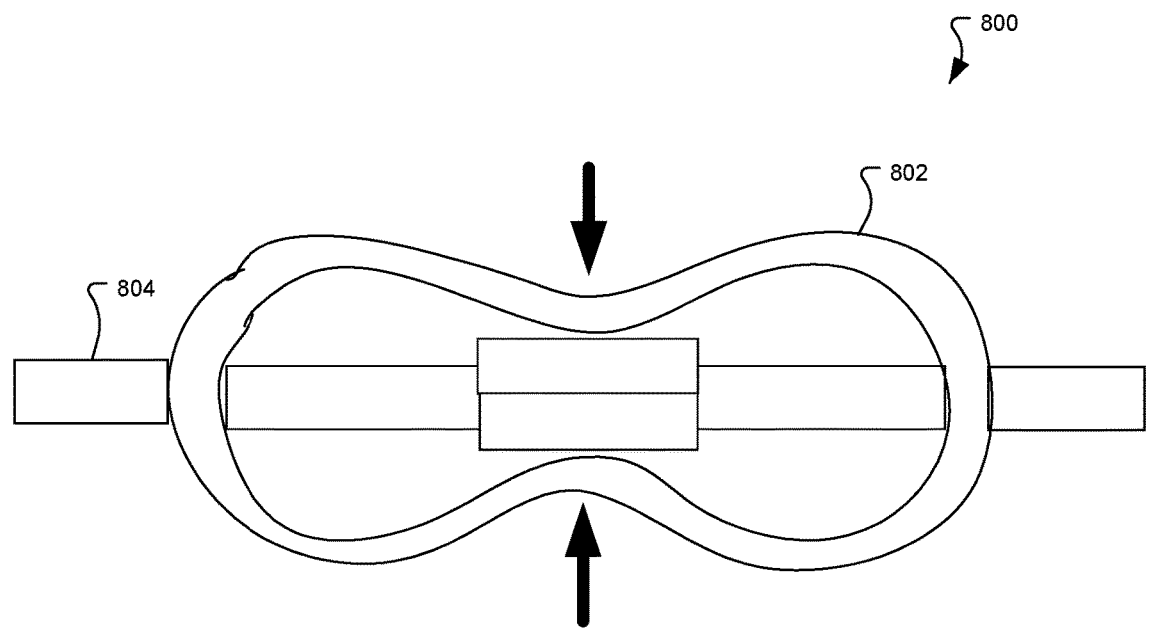

While tubing clamps 180a-180d have been described as including a rectangular-shaped resilient body 300, other shapes can be used. For example, FIGS. 8A and 8B show a tubing clamp 800 with an elliptical-shaped resilient body 802. Other than the elliptical-shaped resilient body 802, tubing clamp 800 is substantially the same as tubing clamps 180a-180d described above. The fluid line 804 passes through openings on the sidewalls of the elliptical-shaped resilient body 802 in substantially the same way as tubing clamp 180.

While the clamp 180a has been described as having certain specific dimensions, other dimensions are possible. For example, the clamp 180a can have a width of 0.60 inches to 0.75 inches, a height of 0.40 inches to 0.55 inches, a length of 1 inch to 2 inches. Additionally, the snap-fit features 308a, 308b can have a length of 0.1 inches to 0.3 inches and a height of 0.1 inches to 0.2 inches.

While the blood treatment system 10 has been described as using four symmetric tubing clamps 180a-180d in addition to the arterial clamp 208 and the venous clamp 218 of the blood treatment machine 100, other clamp arrangements are possible. For example, in some embodiments, the arterial clamp 204 and the venous clamp 218 of the blood treatment machine 100 (as shown in FIGS. 1 and 2) are used to constrict the arterial fluid line 162a and the venous fluid line 162b instead of using the symmetric tubing clamps 180c-180d. In this way, symmetric tubing clamps 180c-180d do not need to be used. Similarly, in some embodiments, the arterial clamp 204 and the venous clamp 218 of the blood treatment machine 100 are not used and instead the symmetric tubing clamps 180c-180d are used to constrict the arterial fluid line 162a and the venous fluid line 162b, respectively.

While the blood treatment system 10 has been described as a hemodialysis system, the symmetric clamps described herein can be used with other types of fluid management systems and blood treatment systems. For example, the symmetric tubing clamps can be used with hemofiltration systems, hemodiafiltration systems, peritoneal dialysis systems, apheresis systems, etc.

Additionally, while the symmetric tubing clamps have been described for use with blood treatment systems, the tubing clamps can alternatively be used in any of various other types of medical systems that include fluid lines, such as infusion pumps, IV pumps, etc. Furthermore, it will be understood that the symmetric tubing clamps described herein are not limited to medical systems. For example, the symmetric tubing clamps can be used in food & beverage tubing systems, fuel & oil tubing systems, and pneumatic & hydraulic tubing systems.

What is claimed is:

1. A tubing clamp comprising:
   a resilient body that has symmetry with respect to a first plane with a normal along a longitudinal axis of the resilient body, the resilient body comprising:
   a sidewall defining an opening such that a tubing is arrangeable through the opening along the longitudinal axis of the resilient body;
   a first snap-fit feature extending inwards from a first face of the resilient body;
   a second snap-fit feature extending inwards from a second face of the resilient body that is opposite the first face of the resilient body, the first snap-fit feature and the second snap-fit feature configured to directly engage with each other when the resilient body is compressed along a direction transverse to the longitudinal axis; and
   a protrusion configured to constrict the tubing when the resilient body is compressed along the direction transverse to the longitudinal axis.

2. The tubing clamp of claim 1, wherein the resilient body symmetry with respect to a second plane with a normal perpendicular to the longitudinal axis.

3. The tubing clamp of claim 1, wherein the protrusion extends transverse to the longitudinal axis of the resilient body.

4. The tubing clamp of claim 1, wherein the protrusion comprises a semi-circular cross section.

5. The tubing clamp of claim 1, wherein the resilient body comprises a face comprising grip features.

6. The tubing clamp of claim 1, wherein the opening is elliptical-shaped.

7. The tubing clamp of claim 1, wherein:
   the first snap-fit feature comprises a first projection and a second projection, the first projection and the second projection each extending inwards from the first face of the resilient body; and
   the second snap-fit feature comprises a third projection and a fourth projection, the third projection and the fourth projection each extending inwards from the second face of the resilient body,
   wherein the first projection is configured to directly engage the third projection when the resilient body is compressed along the direction transverse to the longitudinal axis, and the second projection is configured to directly engage the fourth projection when the resilient body is compressed along the direction transverse to the longitudinal axis.

8. The tubing clamp of claim 1, wherein the first snap-fit feature comprises a first angled face, the second snap-fit feature comprises a second angled face, and the first angled face of the first snap-fit feature and the second angled face of the second snap-fit feature are configured to directly engage with each other when the resilient body is compressed along the direction transverse to the longitudinal axis.

9. A blood treatment system comprising:
   a blood treatment machine; and
   a disposable line set configured to be coupled to the blood treatment machine, the disposable line set comprising:
   a fluid line configured to be connected to a patient for treating blood of the patient; and
   a tubing clamp comprising a resilient body that has symmetry with respect to a first plane with a normal along a longitudinal axis of the resilient body, the resilient body comprising:
   a sidewall defining an opening such that the fluid line of the disposable line set is arranged through the opening along the longitudinal axis of the resilient body;
   a first snap-fit feature extending inwards from a first face of the resilient body;
   a second snap-fit feature extending inwards from a second face of the resilient body that is opposite the first face of the resilient body, the first snap-fit feature and the second snap-fit feature configured to directly engage with each other when the resilient body is compressed along a direction transverse to the longitudinal axis; and
   a protrusion configured to constrict the fluid line of the disposable line set when the resilient body is compressed along the direction transverse to the longitudinal axis.

10. The blood treatment system of claim 9, wherein the resilient body has symmetry with respect to a second plane with a normal perpendicular to the longitudinal axis.

11. A method comprising:
   applying a force to at least one of a top member and a bottom member of a tubing clamp to move the top member and the bottom member of the tubing clamp toward each other to compress a tubing disposed in the tubing clamp and constrict fluid flow within the tubing, directly engaging a first snap-fit feature of the tubing clamp with a second snap-fit feature of the tubing clamp to maintain the compression of the tubing when the force is released, the first snap-fit feature extending inwards from a first face of the tubing clamp and the second snap-fit feature extending inwards from a second face of the tubing clamp that is opposite the first face of the tubing clamp; and shearing the top member relative to the bottom member to release the compression of the tubing and release the constriction of the fluid flow within the tubing.

12. The method of claim 11, wherein the tubing clamp has symmetry with respect to a first plane with a normal direction along a longitudinal axis of the tubing clamp.

13. The method of claim 12, wherein the tubing clamp has symmetry with respect to a second plane with a normal direction perpendicular to the longitudinal axis.

14. The method of claim 11, wherein the movement of the top member and the bottom member of the tubing clamp toward each other generates strain energy within the tubing clamp.

15. The method of claim 14, wherein the movement of the top member and the bottom member of the tubing clamp toward each other is caused by the force being applied in a direction perpendicular to a longitudinal axis of the tubing clamp.

16. The method of claim 11, further comprising moving the top member and the bottom member of the tubing clamp apart from each other after the top member is sheared relative to the bottom member to restore the tubing clamp to an initial position of the tubing clamp.

17. The method of claim 11, wherein the shearing the top member relative to the bottom member causes a displacement of the top member relative to the bottom member along a longitudinal axis of the tubing clamp.

18. The method of claim 11, wherein the shearing the top member relative to the bottom member causes a displacement of the first snap-fit feature relative to the second snap-fit feature.

19. The method of claim 18, wherein the shearing the top member relative to the bottom member causes a disengagement of the first snap-fit feature from the second snap-fit feature.

20. The method of claim 11, further comprising inserting an end of the tubing through an opening at a first end of the tubing clamp and then inserting the end of the tubing through an opening at a second end of the tubing clamp.

* * * * *

UNITED STATES PATENT AND TRADEMARK OFFICE
CERTIFICATE OF CORRECTION

| | | |
|---|---|---|
| PATENT NO. | : 11,975,169 B2 | Page 1 of 1 |
| APPLICATION NO. | : 17/328122 | |
| DATED | : May 7, 2024 | |
| INVENTOR(S) | : Diego Suarez del Real Pena and Nelson Guillermo Santiago Velazquez | |

It is certified that error appears in the above-identified patent and that said Letters Patent is hereby corrected as shown below:

In the Claims

Column 9, Line 66, Claim 2, before "symmetry" insert --has--.

Signed and Sealed this
Second Day of July, 2024

*Katherine Kelly Vidal*

Katherine Kelly Vidal
*Director of the United States Patent and Trademark Office*